United States Patent [19]

Costenzo et al.

[11] Patent Number: 5,498,629

[45] Date of Patent: Mar. 12, 1996

[54] ANTICONVULSANT PSEUDOFRUCTOPYRANOSE SULFAMATES

[75] Inventors: Michael J. Costenzo, Ivyland; Bruce E. Maryanoff, New Hope; David F. McComsey, Warminster; Samuel O. Nortey, LaMott, all of Pa.

[73] Assignee: Ortho Pharmaceutical Corporation, Raritan, N.J.

[21] Appl. No.: 337,597

[22] Filed: Nov. 10, 1994

Related U.S. Application Data

[63] Continuation of Ser. No. 173,399, Dec. 23, 1993, abandoned.

[51] Int. Cl.$^6$ .......... A61K 31/385; A61K 31/335; C07D 327/04; C07D 317/70
[52] U.S. Cl. .......... 514/439; 514/463; 549/31; 549/433
[58] Field of Search .......... 549/31, 433; 514/439, 514/463

[56] References Cited

U.S. PATENT DOCUMENTS

| | | | |
|---|---|---|---|
| 4,075,351 | 2/1978 | Hirsch | 424/303 |
| 4,513,006 | 4/1985 | Maryanoff et al. | 514/23 |
| 4,792,569 | 12/1988 | Maryanoff et al. | 514/517 |

OTHER PUBLICATIONS

McComsey et al., J. Org. Chem. (1994) 59(9), 2652–4.

Primary Examiner—Cecilia Tsang
Attorney, Agent, or Firm—Ralph R. Palo

[57] ABSTRACT

A compound of the general formula I:

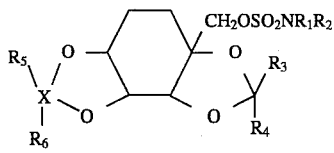

is disclosed as a potent anticonvulsant drug. Pharmaceutical compositions and methods of treatment are also disclosed.

9 Claims, No Drawings

ANTICONVULSANT PSEUDOFRUCTOPYRANOSE SULFAMATES

This application is a Continuation of U.S. Ser. No. 08/173,39 which is filed Dec. 23, 1993, now abandoned.

BACKGROUND OF THE INVENTION

Sulfamates of various structures, including those derived from monosaccharides, are described in *J. Med. Chem.* 1987, 30, 880 and in U.S. Pat. No. 4,075,351. Certain of these sulfamates are useful as pharmaceutical agents. More recently, sulfamates having various pharmaceutical activity in the areas of epilepsy, glaucoma, peptic ulcers, and male infertility are described in U.S. Pat. Nos. 4,513,006, 4,459,601 and 4,792,569. One of the compounds covered by U.S. Pat. No. 4,513,006, topiramate, has not only been found to exhibit particularly significant anticonvulsant activity in animals, but also appears to be useful in humans for the treatment of epilepsy (*Drugs Future* 1989, 14, 342).

While sulfamate compounds of the type disclosed in U.S. Pat. No. 4,513,006 have been shown to exhibit useful biological activity when administered to mammals, other compounds with equal or improved activity compared to topiramate would be desirable.

Replacement of the ring oxygen of cyclic monosaccharides by a methylene group affords an interesting class of compounds which has been referred to as "pseudo-sugars". These cyclotol compounds possess enhanced biological activity compared to the original monosaccharides.

Accordingly, it is an object of the present invention to describe novel pseudo-β-fructopyranose sulfamate derivatives, which are related to topiramate, with potent anticonvulsant activity.

SUMMARY OF THE INVENTION

It has been found that certain sulfamate derivatives represented by the general formula I:

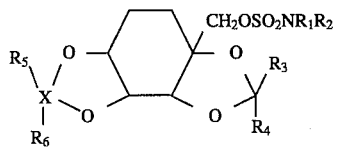

wherein $R_1$, $R_2$, $R_3$, $R_4$, $R_5$ and $R_6$ and X are as defined hereinafter exhibit anticonvulsant activity. As a result, the compounds and pharmaceutical compositions containing such compounds of the present invention are useful for the treatment of convulsions such as epileptic seizures.

DETAILED DESCRIPTION OF THE INVENTION

More particularly, the present invention is directed to compounds represented by the following formula I:

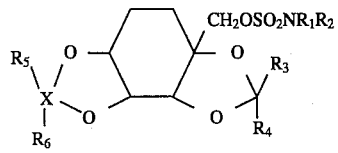

wherein $R_1$ and $R_2$ are the same or different and are selected from any of hydrogen, alkyl ($C_1$ to $C_6$), cycloalkyl ($C_3$–$C_7$), allyl, or benzyl. Preferably, $R_1$ and $R_2$ are each hydrogen.

$R_3$ and $R_4$ are the same or different and selected from hydrogen or lower alkyl.

X may be chosen from carbon (C) or sulfur (S), with the stipulation that when X is carbon $R_5$ and $R_6$ are the same or different and are selected from hydrogen or lower alkyl, whereas when X is sulfur one of $R_5$ and $R_6$ is oxygen and the other is a lone pair of electrons or both are oxygen.

As used herein, the term alkyl includes straight and branched chains. For example, alkyl radicals include methyl, ethyl, propyl, isopropyl, n-butyl, isobutyl, and t-butyl.

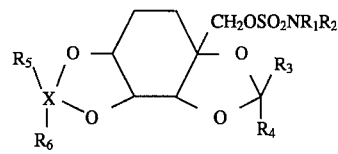

wherein $R_1$, $R_2$, $R_3$, $R_4$, $R_5$ and $R_6$ and X are as defined hereinafter exhibit anticonvulsant activity. As a result, the compounds and pharmaceutical compositions containing such compounds of the present invention are useful for the treatment of convulsions such as epileptic seizures.

DETAILED DESCRIPTION OF THE INVENTION

More particularly, the present invention is directed to compounds represented by the following formula I:

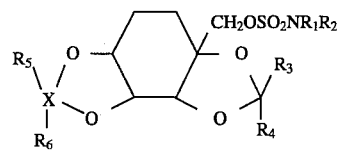

wherein $R_1$ and $R_2$ are the same or different and are selected from any of hydrogen, alkyl ($C_1$ to $C_6$), cycloalkyl ($C_3$–$C_7$), allyl, or benzyl. Preferably, $R_1$ and $R_2$ are each hydrogen.

$R_3$ and $R_4$ are the same or different and selected from hydrogen or lower alkyl.

X may be chosen from carbon (C) or sulfur (S), with the stipulation that when X is carbon $R_5$ and $R_6$ are the same or different and are selected from hydrogen or lower alkyl, whereas when X is sulfur one of $R_5$ and $R_6$ is oxygen and the other is a lone pair of electrons or both are oxygen.

As used herein, the term alkyl includes straight and branched chains. For example, alkyl radicals include methyl, ethyl, propyl, isopropyl, n-butyl, isobutyl, and t-butyl.

Particularly preferred compound of formula 1 are:
- (1R,2R,3S,4S)-(1,2:3,4-di-O-methylethylidenecyclohexan-1,2,3,4-tetraol-4-yl)methyl sulfamate, i.e., where $R_1$ and $R_2$ are hydrogen, $R_3$, $R_4$, $R_5$, and $R_6$ are methyl and X is carbon in formula I.
- (1R,2S,3S,4S)-(3,4-0-methylethylidene-1,2-O-sulfinylcyclohexan-1,2,3,4-tetraol-4-yl)methyl sulfamate, i.e., where $R_1$ and $R_2$ are hydrogen, $R_3$ and $R_4$ are methyl, $R_5$ is oxygen and $R_6$ is an electron pair and X is sulfur in formula I.
- (1R,2S,3S,4S)-(3,4-O-methylethylidene- 1,2-O-sulfonylcyclohexan-1,2,3,4-tetraol-4-yl)methyl sulfamate, i.e., where $R_1$ and $R_2$ are hydrogen, $R_3$ and $R_4$ are methyl, $R_5$ and $R_6$ are both oxygen and X is sulfur in formula I.

Included within the scope of this invention are the various individual anomers, diastereomers and enantiomers as well as mixtures thereof. Such compounds are included within the definition of formula I. In addition, the compounds of this invention include pharmaceutically acceptable salts, for example; alkali metal salts, such as sodium or potassium, ammonium salts, dialkylammonium salts, trialkylammonium salts, tetraalkylammonium salts, and tromethamine salts. Hydrates and other solvates of the compound of the formula I are also included within the scope of this invention.

Compounds of formula I may be prepared as outlined in the following schemes.

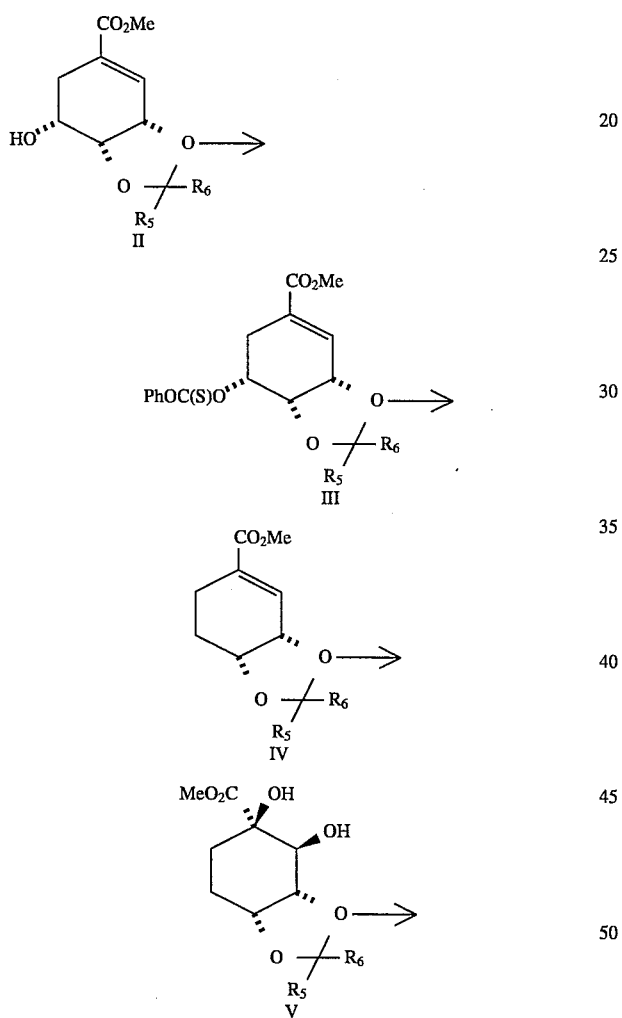
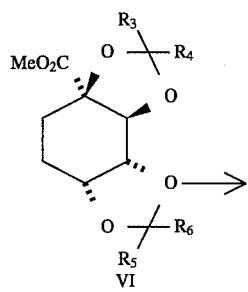
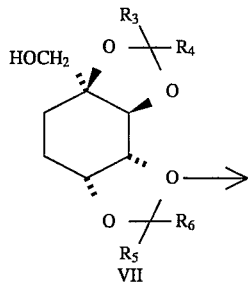
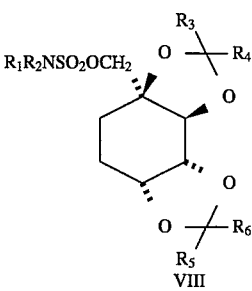

Scheme 2

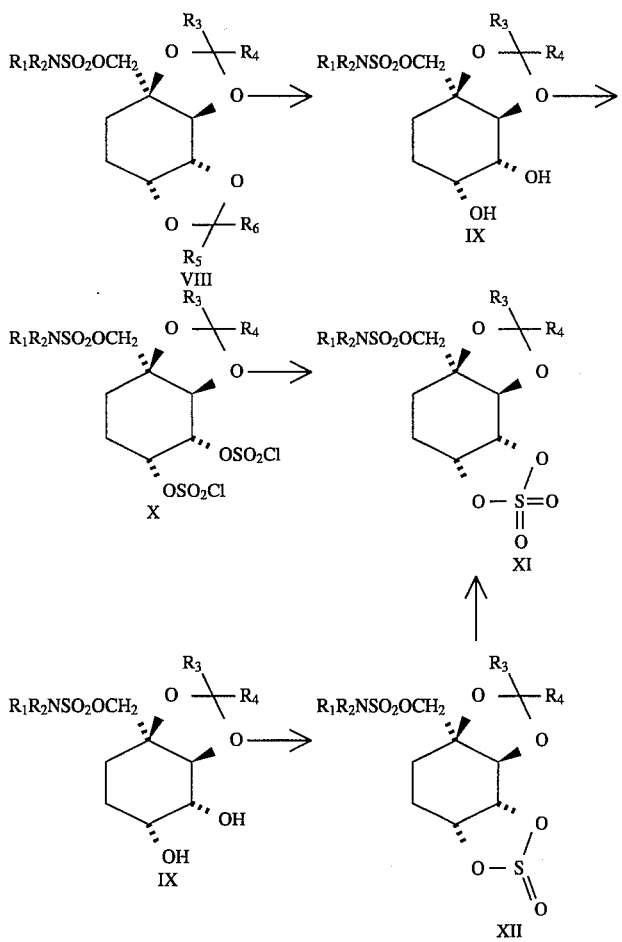

More specifically, the alcohol II, wherein $R_5$ and $R_6$ are methyl, (prepared according to the method of Shing, T. K. and Tang, Y. *Tetrahedron* 1990, 46, 6575–6584) is treated with a mixture of phenyl chlorothionoformate and pyridine and a catalytic amount of 4dimethylaminopyridine in an appropriate solvent such as methylene chloride for 2 h at room temperature to give thionocarbonate III ($R_5=R_6=$Me). This carbonate is reduced with tributyltin hydride under free radical conditions using tert butyl peroxide in toluene at reflux for 2 h to give the ester IV ($R_5=R_6=$Me).

The diol V ($R_5=R_6=$Me) is prepared by combining IV ($R_5=R_5=$Me) with trimethylamine oxide, pyridine, water, and osmium tetroxide in t-butanol at reflux for 2 h. This diol is treated with 2-methoxypropene and an acid catalyst such as camphorsulfonic acid in a suitable solvent such as methylene chloride at room temperature for 2–6 h to afford bis-acetonide VI ($R_3$, $R_4$, $R_5$, $R_6=$Me ).

Reduction of VI ($R_3$, $R_4$, $R_5$, $R_6=$Me) with diisobutylaluminum hydride at $-20°$ C. to room temperature in a suitable solvent such as tetrahydrofuran gave alcohol VII ($R_3$, $R_4$, $R_5$, $R_6=$Me). Sulfamate VIII ($R_1=R_2=$H; $R_3$, $R_4$, $R_5$, $R_6=$Me) was prepared by treating VII ($R_3$, $R_4$, $R_5$, $R_6=$Me) with sulfamoyl chloride and triethylamine in a suitable solvent such as methylene chloride at 0° C. for 2–6 h.

Preparation of diol IX ($R_1=R_2=$H; $R_3=R_4=$Me) may be accomplished (see *J. Med. Chem.* 1987, 30, 880) by the hydrolysis of VIII ($R_1=R_2=$H; $R_3$, $R_4$, $R_5$, $R_6=$Me) using an acid catalyst such as HCl in a suitable solvent such as THF or ethanol at room temperature to reflux for 2–6 h. Treatment of IX ($R_1=R_2=$H; $R_3=R_4=$Me) with sulfuryl chloride in the presence of pyridine or triethylamine at -78° C. to 25° C. in a suitable solvent such as methylene chloride or toluene (see U.S. Pat. No. 5,242,942) affords the bis-chlorosulfate X ($R_1=R_2=$H; $R_3=R_4=$Me). Reaction of X with a weak base such as $NaHCO_3$ or pyridine in an alcohol solvent such as ethanol at $-40°$ C. to 25° C. yields the cyclic sulfate XI ($R_1=R_2=$H; $R_3=R_4=$Me).

Preparation of cyclic sulfite XII ($R_1=R_2=$H; $R_3=R_4=$Me) may be accomplished (see U.S. Pat. No. 5,242,942) by reaction of IX ($R_1=R_2=$H; $R_3=R_4=$Me) with thionyl chloride with or without a weak base such as pyridine in a suitable solvent such as methylene chloride, dioxane or ethyl acetate at $-20°$ C. to 25° C. Futhermore, cyclic sulfite XII ($R_1=R_2=$H; $R_3=R_4$ =Me) may be oxidized to the cyclic sulfate XI ($R_1=R_2=$H; $R_3=R_4=$Me) with a suitable oxidizing agent such as ruthenium tetroxide in a suitable solvent such as methylene chloride or benzene.

Pharmaceutically acceptable salts of the compounds of formula (I) may be prepared by reacting the sulfamate of formula (I) with an appropriate base and recovering the salt.

The compounds of formula I are particularly useful as anticonvulsant agents in mammals including humans. The anticonvulsant activity of the subject compounds was determined using a standard "maximal electroshock test" (MES). In this test, activity is indicated by a block of the toxic extensor seizure caused by application of an electric shock to mice via corneal electrodes, as described by Swinyard et al. in *J. Pharmacol. Expt. Ther.* 1952, 106, 319, and recorded as % block. A more recent description of current anticonvulsant drug screening is given by Swinyard in *Epilepsia* 1978, 19, 409.

In the test, albino male CRS-CD1 mice weighing between 18–25 g were used in all experiments (obtained from Charles River). They were allowed food and water ad libitum and were used only once. The electroshock apparatus and the corneal electrodes were purchased from Wahlquist Instrument Company, Salt Lake City, Utah. Maximal electroshock seizures were induced by the delivery of a 60 Hertz (Hz) current of 50 milliamps (mA) intensity to the mouse through corneal electrodes for 0.2 seconds as originally described by Swinyard (1952). This stimulus intensity is approximately 4 to 6 times the current producing 100% tonic extensor convulsions. During the validation of the MES test, the duration of the various seizure components following maximal electroshock was measured as follows: hindleg tonic flexion was measured from the time of the application of the stimulus to the time of onset of hindleg tonic extension (i.e. when the hindlegs deviate by greater than an angle of 90° from the torso), hindleg tonic extensor was measured from the time of extensor thrust to the onset of generalized clonus, and terminal clonus was measured from the beginning to the end of bilateral rhythmic clonic jerking. Mortality was also recorded. The duration of each seizure component agreed well with the values previously reported by Tedeschi et al. in *J. Pharmacol. Expt. Ther.* 1955, 116, 107. The corneal electrodes were concave so that saline could be applied to the electrodes to reduce mortality. If this procedure is followed, mortality should always be less than 40% in control mice. Thus, at an electroshock stimulus of 60 Hz, 50 mA and 0.2 seconds duration, the order of convulsive components and the percentage of control animals displaying the behaviors should be as follows: tonic flexion (100%), tonic extension (100%) and clonus (100%) with less than 40% morality.

For testing compounds, the abolition of the tonic extensor component was the endpoint. Animals were dosed orally (PO) with either vehicle or test drug and at a specified time were given a maximal electric shock through corneal electrodes blotted with saline (as described above). A minimum of 10 animals were used per group and the percentage of animals in the group without tonic hindlimb extension recorded. Determination of an $ED_{50}$ dose (that dose which inhibits 50% of the tonic extension seizures) was made. For example, the anticonvulsant activity of compound of formula I wherein $R_1$ and $R_2$ are hydrogen, $R_3$, $R_4$, R5, and $R_6$ are methyl and X is carbon gave an $ED_{50}$ of 16 mg/kg in mice at 4 hours following oral dosing.

For treating epilepsy, a compound of formula I may be employed at a daily dosage in the range of about 10 to 2000 mg, usually in 1 to 4 daily divided doses, for an average adult human. A unit dose would contain about 5 to 500 mg of the active ingredient. This translates to a dose of about 0.1 to 30 mg/kg/day.

In general, compounds of formula i may be used in treating epilepsy in a manner similar to that used for phenytoin; e.g., orally administering a solid formulation twice/day. Medical aspects of the treatment of epilepsy are described in greater detail by L. S. Goodman et al. in "The Pharmacological Basis of Therapeutics", 5th Ed. pages 201 to 226, Macmillan (1975).

The compounds of formula I preferably are administered in the form of a pharmaceutical composition. To prepare the pharmaceutical compositions of this invention, one or more sulfamate compounds of formula I are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carder will usually comprise sterile water, though other ingredients, for purposes such as aiding solubility or for preservation, may be included. Injectable suspensions may also be prepared, in which case appropriate liquid carriers, suspending agents, and the like may be employed.

It is especially advantageous to formulate the aforementioned pharmaceutical compositions in unit dosage form for ease of administration and uniformity of dosage. The term "unit dosage form" as used in the specification and claims herein refers to physically discrete units suitable as unit dosages, each unit containing a predetermined quantity of active ingredient calculated to produce the desired therapeutic effect in association with the required pharmaceutical carrier.

The pharmaceutical compositions herein will contain, per unit dosage, e.g., tablet, capsule, powder, injection, teaspoonful, suppository and the like. The compositions will be administrated in amounts as previously described herein with regard to the active ingredient and to the condition being treated. The dosages, however, may be varied depending upon the requirement of the patient, the severity of the condition being treated, and the compound being employed. Determination of optimum dosages for a particular situation is within the skill of the art.

In the following Example and throughout the specification the following terms and abbreviations are used: g (grams); mL (milliliters); min (minutes); h (hours); mol (moles); mmol (millimoles); M (molar); v/v (volume to volume); TLC (thin layer chromatography); HPLC (high pressure liquid chromatography); C, H, N, etc. (the chemical symbols for the elements); Anal. Calcd. (analysis calculated); $[\alpha]D^{25}$ (specific rotation measured at 25 ° C. with 589 nanometer light ); c (concentration in grams per 100 mL); $^1H$ NMR (proton nuclear magnetic resonance spectrum); NMR abbreviations: s=singlet, d=doublet, t=triplet, m=multiplet, br=broadened, dd=doublet of doublets; CI-MS (chemical ionization mass spectrum); mp (melting point). All melting points are corrected.

EXAMPLE 1:

(1R,2R,3S,4S)-[1,2:3,4-Di-O-(1-methylethylidene)cyclohexan-1,2,3,4-tetraol-4-yl] methyl sulfamate. [VIII ($R_1$=$R_2$=H: $R_3$, $R_4$, $R_5$, $R_6$=Me) ].

(1R,2R,3S)-2,3-O-(1-Methylethylidene )-5-methoxycarbonyl-4-cyclohexen- 1,2,3-triol (1.56 g, 6.8 mmol; prepared according to the method of Shing, T. K. and Tang, Y. *Tetrahedron* 1990, 46, 6575–6584), pyridine (2.16 g, 27 mmol) and a catalytic amount of 4-dimethylaminopyridine were dissolved in methylene chloride (35 mL) and at 23° C. phenyl chlorothionoformate (1.77 g, 10.2 mmol) was added slowly under argon. After 2 h, the reaction was poured into saturated ammonium chloride (200 mL) and diluted with methylene chloride. The organic layer was separated, washed with brine, dried ($MgSO_4$), and evaporated in vacuo to a yellow oil, which was purified by preparative HPLC (ethyl acetate/hexane, 1:8) to afford a white solid. Recrystallization from methylene chloride/2-propanol gave analytically pure white solid thionocarbonate III ($R_5=R_6$=Me): mp 123°–125° C.; CI-MS ($CH_4$) MH+=365; $^1$H NMR $\delta 1.42$ (s, $CH_3$), 1.45 (s, $CH_3$), 2.77 (m, 1 H, $H_{6a}$), 3.00 (dd, J=16.5, 5.5 Hz, $H_{6e}$), 3.80 (s, $OCH_3$), 4.67 (br d, J=3.4 Hz, $H_3$), 4.85 (br m, 1 H, $H_2$), 5.60 (ddd, J=10.1, 5.5, 2.3 Hz, $H_1$), 6.81 (m, 1.0H, $H_4$), 7.13 (dd, 2H, J=7.4, 1.2 Hz, ortho arom.), 7.31 (dd, 1 H, J=7.3, 7.4 Hz, para arom.), 7.43 (dd, 2H, J=7.4, 8.0 Hz, meta arom.); $[\alpha]D^{20}$–6.07 (c=0.692, $CH_3OH$). Anal. Calcd for $C_{18}H_{20}O_6S$: C, 59.33; H, 5.53. Found: C, 59.22; H, 5.48.

Thionocarbonate III ($R_5=R_6$=Me; 1.53 g, 4.2 mmol), tributyltin hydride (1.83 g, 6.3 mmol), and tert-butyl peroxide (123 mg, 0.84 mmol) were combined in toluene (80 mL) and heated at reflux for 1.5 h. Upon cooling, the reaction was evaporated in vacuo to a clear oil, which was dissolved in diethyl ether (100 mL). The ether solution was washed once with 1 M NaOH (100 mL), water (50 mL), brine (50 mL), dried ($MgSO_4$), and evaporated in vacuo to give crude product. This was purified by preparative HPLC (ethyl acetate/hexane, 1:8) to afford ester IV ($R_5=R_6$=Me) as a clear oil: CI-MS ($CH_4$) MH+=213; $^1$H NMR $\delta 1.37$ (s, $CH_3$), 1.39 (s, $CH_3$), 1.80 (m, 1H, $H_{6a}$), 2.05 (m, 1H, $H_{5a}$), 2.25–2.45 (m, 2H, $H_{5e}/H_{6e}$), 3.76 (s, $OCH_3$), 4.35 (ddd, J=3.0, 5.4, 5.4 Hz, $H_1$), 4.59 (m, $H_2$), 6.78 (br s, 0.95 H, $H_3$).

The ester IV ($R_5=R_6$=Me; 0.66 g, 3.1 mmol) was combined with trimethylamine oxide dihydrate (0.49 g, 4.40 mmol), pyridine (1.50 g, 18.8 mmol), and water (0.30 g, 16.8 mmol) in tert-butanol (30 mL) and osmium tetroxide (30 mg, 0.12 mmol) was then added at 23° C. The reaction was heated at reflux for 2 h, cooled, and diluted with 20% $NaHSO_3$ (15 mL), and stirred for 30 min at 23° C. The solution was evaporated in vacuo to a residue, which was partitioned between water and ethyl acetate. The organic extract was washed with brine, dried ($MgSO_4$), and evaporated in vacuo to give a light yellow oil, diol V ($R_5=R_6$=Me): CI-MS ($CH_4$) MH+=247; $^1$H NMR $\delta 1.39$ (s, $CH_3$), 1.55 (s, $CH_3$), 1.65 (m, 1H, $H_{6a}$), 2.0–2.2 (m, 3H, $H_{6e}/H_{5a}/H_{5e}$), 2.28 (d, J=7.2 Hz, OH), 3.28 (s, OH), 3.88 (dd, J=7.3, 7.5 Hz, $H_3$), 3.98 (dd, J=5.1, 7.7 Hz, $H_2$), 4.45 (m, 1H, H1).

2-Methoxypropene (0.26 g, 3.6 mmol) was added to the diol V ($R_5=R_6$=Me; 0.44 g, 1.8 mmol) in methylene chloride (10 mL) under argon, followed by a catalytic amount of camphorsulfonic acid. After 1.5 h, another equivalent of 2-methoxypropene (0.13 g, 1.8 retool) was added and stirring was continued for 1 h. Saturated $NaHCO_3$ (5 mL) was added and the organic phase was separated, washed with brine, dried ($MgSO_4$), and evaporated in vacuo to give crude bis-acetonide VI ($R_3, R_4, R_5, R_6$=Me), as an oil: CI-MS ($CH_4$) MH+=287; $^1$H NMR $\delta 1.34$ (s, $CH_3$), 1.35 (s, $CH_3$), 1.47 (s, $CH_3$), 1.48 (s, $CH_3$), 1.60–1.90 (m, 3H, $H_{5e}/H_{6e}/H_{6a}$), 2.00 (ddd, J=5.3, 15.0, 15.0 Hz, $H_{5a}$), 3.80 (s, $OCH_3$), 4.43 (m, $H_1$), 4.50 (dd, J=2.2, 7.6 Hz, $H_2$), 4.71 (d, J=2.2 Hz, $H_3$).

This bis-acetonide VI ($R_3, R_4, R_5, R_6$=Me; 390 mg, 1.36 mmol)in tetrahydrofuran (7.0 mL) was cooled to -20° C. (ice/methanol bath) and diisobutylaluminum hydride (DIBAL-H, 2.75 mL, 1 M in THF) was added over 15 min and the reaction was allowed to come to 23° C. After 30 min, the reaction was cooled again to –10° C. and another portion of DIBAL-H (2.75 mL) was added. When the reaction was complete (TLC), saturated ammonium chloride (10 mL) was added to the ice-cooled reaction and it was stirred for 10 min. The mixture was evaporated in vacuo and the residue was extracted three times with chloroform (50 mL). The organic phase was washed with brine, dried ($MgSO_4$) and evaporated in vacuo to a clear oil. This was purified by preparative TLC (ethyl acetate/hexane, 1:2) to afford the alcohol VII ($R_3, R_4, R_5, R_6$=Me), as a clear viscous oil: CI-MS ($CH_4$) MH+=259; $^1$H NMR $\delta 1.34$ (s, $CH_3$), 1.40 (s, $CH_3$), 1.46 (s, $CH_3$), 1.47 (s, $CH_3$), 1.60–1.95 (m, 4 aliphatics), 2.08 (dd, J=5.7, 7.2 Hz, OH), 3.55 (m, 2H, $CH_2O$), 4.27 (d, J=2.7 Hz, $H_3$), 4.44 (m, 1 H, $H_1$), 4.54 (dd, J= 2.7, 7.5 Hz, $H_2$).

The alcohol VII ($R_3, R_4, R_5, R_6$=Me; 0.24 g, 0.93 mmol) and triethylamine (0.20 g, 2 mmol) were combined in dimethylformamide (6 mL) and cooled to 0° C. under argon. Sulfamoyl chloride (0.215 g, 1.86 mmol) was added and the reaction stirred for 2 h at 0° C., whereupon additional triethylamine (0.20 g, 2 mmol) and sulfamoyl chloride (0.215 g, 1.86 mmol) were added; stirring was continued for 1 h at 0° C. The reaction was partitioned between methylene chloride and dilute $NaHCO_3$ and the organic phase was separated and washed three times with water, once with brine, dried ($MgSO_4$), and evaporated in vacuo to give a viscous oil. The product was purified by preparative TLC (ethyl acetate/hexane, 1:2) to afford viscous oil sulfamate VIII ($R_1=R_2$=H; $R_3, R_4, R_5, R_6$=Me): CI-MS ($NH_3$) MH+= 338; $^1$H NMR $\delta 1.34$ (s, $CH_3$), 1.44 (s, $CH_3$), 1.45 (s, $CH_3$), 1.47 (s, $CH_3$), 1.60–1.90 (m, 4 aliphatics), 4.16 (d, J=11.1 Hz, $CH_aOSO_2$), 4.21 (d, J=2.6 Hz, $H_3$), 4.29 (d, J=11.1 Hz, $CH_bOSO_2$), 4.44 (br d, J=7.5 Hz, $H_1$), 4.53 (dd, J=2.6, 7.5 Hz, $H_2$), 4.95 (br s, $NH_2$); $[\alpha]D^{25}$ +1.20 (c =0.5, $CH_3OH$). Anal. Calcd for $C_{13}H_{23}NO_7S$: C, 46.28; H, 6.87; N, 4.15. Found: C, 46.08; H, 6.89; N, 4.19.

EXAMPLE 2

(1R,2R,3S,4S)-[1,2:3,4-Di-O-(1-methylethylidene)cyclohexan 1,2,3,4-tetraol-4-yl] methyl dimethylsulfamate. [VIII ($R_1, R_2, R_3, R_4, R_5, R_6$=Me)].

The alcohol VII, prepared above in Example 1, ($R_3, R_4, R_5, R_6$=Me; 0.24 g, 0.93 mmol) and triethylamine (0.20 g, 2 mmol) are combined in dimethylformamide (6 mL) and the solution is cooled to 0° C. under argon while diethylsulfamoyl chloride (0.275 g, 1.86 mmol) is added. After 3 h at 0° C., the reaction is partitioned between methylene chloride and $NaHCO_3$. The organic solution is separated and washed three times with water, once with brine, dried ($MgSO_4$) and evaporated in vacuo to a viscous oil. The product is purified by preparative TLC (ethyl acetate/hexane) and gives sulfamate VIII ($R_1, R_2, R_3, R_4, R_5, R_6$=Me).

EXAMPLE 3

(1R,2S,3S,4S)-[3,4-O-(1-methylethylidene)-1.2-O-sulfonylcyclo-hexan-1.2.3.4-tetraol-4-yl)methyl sulfamate, [XI ($R_1, R_2$=H; $R_3, R_4$=Me)].

Sulfamate VIII ($R_1=R_2$=H; $R_3, R_4, R_5, R_6$=Me; 0.38 g, 1.0 mmol) in THF (5 mL) and 3N HCl (5 mL) is stirred at 45° C. for 4 h. The solution is cooled to room temperature and adjusted to pH 7.0 with Na₂CO₃ and extracted with THF three times. The organic solution is dried (MgSO₄) and evaporated in vacuo to oily IX ($R_1, R_2$=H; $R_3, R_4$=Me). This diol is dissolved in ethyl acetate (10 mL) and pyridine (3 mL), cooled to -60° C. and is treated with sulfuryl chloride (0.30 g, 2.24 mmol) and stirred at room temperature for 3 h. White solid is filtered and the filtrate is washed once with 1N HCl, once with saturated NaHCO₃, once with brine, dried (MgSO₄) and evaporated in vacuo and gives bis chlorosulfate X ($R_1, R_2$=H; $R_3, R_4$=Me). This bis chlorosulfate in methanol (3 mL) is combined with NaHCO₃ (0.504 g, 6.0 mmol) and is stirred at room temperature for 24 h. The reaction is filtered and evaporated in vacuo. The residue is dissolved in ethyl acetate and washed with brine, dried (MgSO₄) and evaporated in vacuo to give cyclic sulfate XI ($R_1, R_2$=H; $R_3, R_4$=Me).

EXAMPLE 4

(1R,2S,3S,4S)-[3.4-O-(1-methylethylidene)-1.2-O-sulfinylcyclo-hexan-1,2,3,4-tetraol-4-yl)methyl sulfamate. [XII ($R_1, R_2$=H; $R_3, R_4$=Me)].

Diol IX (R1, $R_2$=H; $R_3, R_4$=Me) (0.30 g, 1.0 mmol)in dioxane (5mL) is heated at reflux as thionyl chloride (1.5 mL, 20 mmol) is added in. After 15 rain, the reaction is cooled and evaporated in vacuo. The residue is dissolved in ethyl acetate and washed twice with saturated NaHCO₃, twice with brine, dried (MgSO₄) and evaporated in vacuo to cyclic sulfite XII ($R_1, R_2$=H; $R_3, R_4$=Me).

What is claimed is:

1. A compound represented by the formula I:

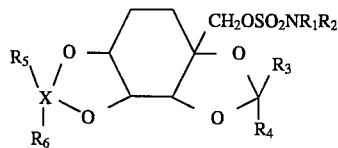

wherein $R_1$ and $R_2$ are the same or different and are selected from any of hydrogen, alkyl ($C_1$ to $C_6$), cycloalkyl ($C_3$-$C_7$), allyl, or benzyl;

$R_3$ and $R_4$ are the same or different and selected from hydrogen or lower alkyl;

X may be chosen from carbon (C) or sulfur (S), with the stipulation that when X is carbon $R_5$ and $R_6$ are the same or different and are selected from hydrogen or lower alkyl, whereas when X is sulfur one of $R_5$ and $R_6$ is oxygen and the other is a lone pair of electrons or both are oxygen; or the pharmaceutically acceptable salt, hydrate, anomer, diastereomer, or enanantiomer thereof.

2. The compound of claim 1, wherein $R_1$ and $R_2$ are each hydrogen.

3. The compound of claim 1, wherein X is carbon.

4. The compound of claim 1, wherein X is sulfur.

5. The compound of claim 4, wherein $R_5$ and $R_6$ are each oxygen.

6. The compound of claim 4, wherein $R_5$ and $R_6$ are a lone pair of electrons and oxygen.

7. The compound of claim 1, selected from any of (1R,2R,3S,4S)-(1,2:3,4-di-O-methylethylidenecyclohexan- 1,2,3,4-tetraol-4-yl)methyl sulfamate, i.e., where $R_1$ and $R_2$ are hydrogen, $R_3, R_4, R_5$, and $R_6$ are methyl and X is carbon in formula I.

(1R,2S,3S,4S)-(3,4-O-methylethylidene-1,2-O-sulfinyl-cyclohexan 1,2,3,4-tetraol-4-yl)methyl sulfamate, i.e., where $R_1$ and $R_2$ are hydrogen, $R_3$ and $R_4$ are methyl, $R_5$ is oxygen and $R_6$ is an electron pair and X is sulfur in formula I.

8. A pharmaceutical composition for treating convulsions comprising the compound of claim 1, in combination with a pharmaceutically acceptable carrier, said compound being present in a therapeutically effective amount for treating convulsions.

9. A method of treating an animal suffering from convulsions comprising treating that animal with the compound of claim 1 in an amount sufficient to treat the convulsions.

* * * * *